(12) United States Patent
Wasserman et al.

(10) Patent No.: US 12,431,459 B2
(45) Date of Patent: Sep. 30, 2025

(54) METHODS OF MONITORING GAS BYPRODUCTS OF A BONDING SYSTEM, AND RELATED MONITORING SYSTEMS AND BONDING SYSTEMS

(71) Applicant: Kulicke and Soffa Industries, Inc., Fort Washington, PA (US)

(72) Inventors: Matthew B. Wasserman, Fort Washington, PA (US); Thomas J. Colosimo, Jr., Fort Washington, PA (US)

(73) Assignee: Kulicke and Soffa Industries, Inc., Fort Washington, PA (US)

( * ) Notice: Subject to any disclaimer, the term of this patent is extended or adjusted under 35 U.S.C. 154(b) by 444 days.

(21) Appl. No.: 18/108,725

(22) Filed: Feb. 13, 2023

(65) Prior Publication Data

US 2023/0260953 A1 Aug. 17, 2023

Related U.S. Application Data

(60) Provisional application No. 63/311,018, filed on Feb. 16, 2022.

(51) Int. Cl.
*H01L 23/00* (2006.01)
*B01D 53/40* (2006.01)

(52) U.S. Cl.
CPC .............. *H01L 24/75* (2013.01); *B01D 53/40* (2013.01); *H01L 24/81* (2013.01); *B01D 2258/0216* (2013.01); *H01L 2224/751* (2013.01); *H01L 2224/759* (2013.01); *H01L 2224/81065* (2013.01); *H01L 2224/81203* (2013.01); *H01L 2224/81908* (2013.01); *H01L 2224/81986* (2013.01); *H01L 2924/40* (2013.01)

(58) Field of Classification Search
CPC ... H01L 24/75; H01L 24/81; H01L 2224/751; H01L 2224/759; H01L 2224/81065; H01L 2224/81203; H01L 2224/81908; H01L 2224/81986; H01L 2924/40; B01D 53/40; B01D 2258/0216; G01N 21/3504; G01N 2021/3595; G01N 33/0009; G01N 33/0021
USPC ........................................................ 438/455
See application file for complete search history.

(56) References Cited

U.S. PATENT DOCUMENTS

| | | | |
|---|---|---|---|
| 10,861,820 B2 | 12/2020 | Bajwa | |
| 11,205,633 B2 | 12/2021 | Bajwa et al. | |
| 2019/0252349 A1* | 8/2019 | Bajwa | H01L 24/75 |
| 2020/0294960 A1* | 9/2020 | Miyazaki | B23K 1/20 |

FOREIGN PATENT DOCUMENTS

| | | | | |
|---|---|---|---|---|
| JP | 2010045071 A | * | 2/2010 | |
| JP | 2011121102 A | * | 6/2011 | |

* cited by examiner

*Primary Examiner* — Norman D Richards
*Assistant Examiner* — Laura M Dykes
(74) *Attorney, Agent, or Firm* — Christopher M. Spletzer, Sr.

(57) ABSTRACT

A method of monitoring gas byproducts of a bonding system is provided. The method includes: providing a plurality of bonding systems, each of the bonding systems including a reducing gas delivery system for use in connection with a bonding operation, each of the bonding systems being configured for exhausting gas byproducts; connecting each of the bonding systems to a monitoring device using a respective gas delivery path; and monitoring a composition of at least a portion of the gas byproducts with the monitoring device.

26 Claims, 12 Drawing Sheets

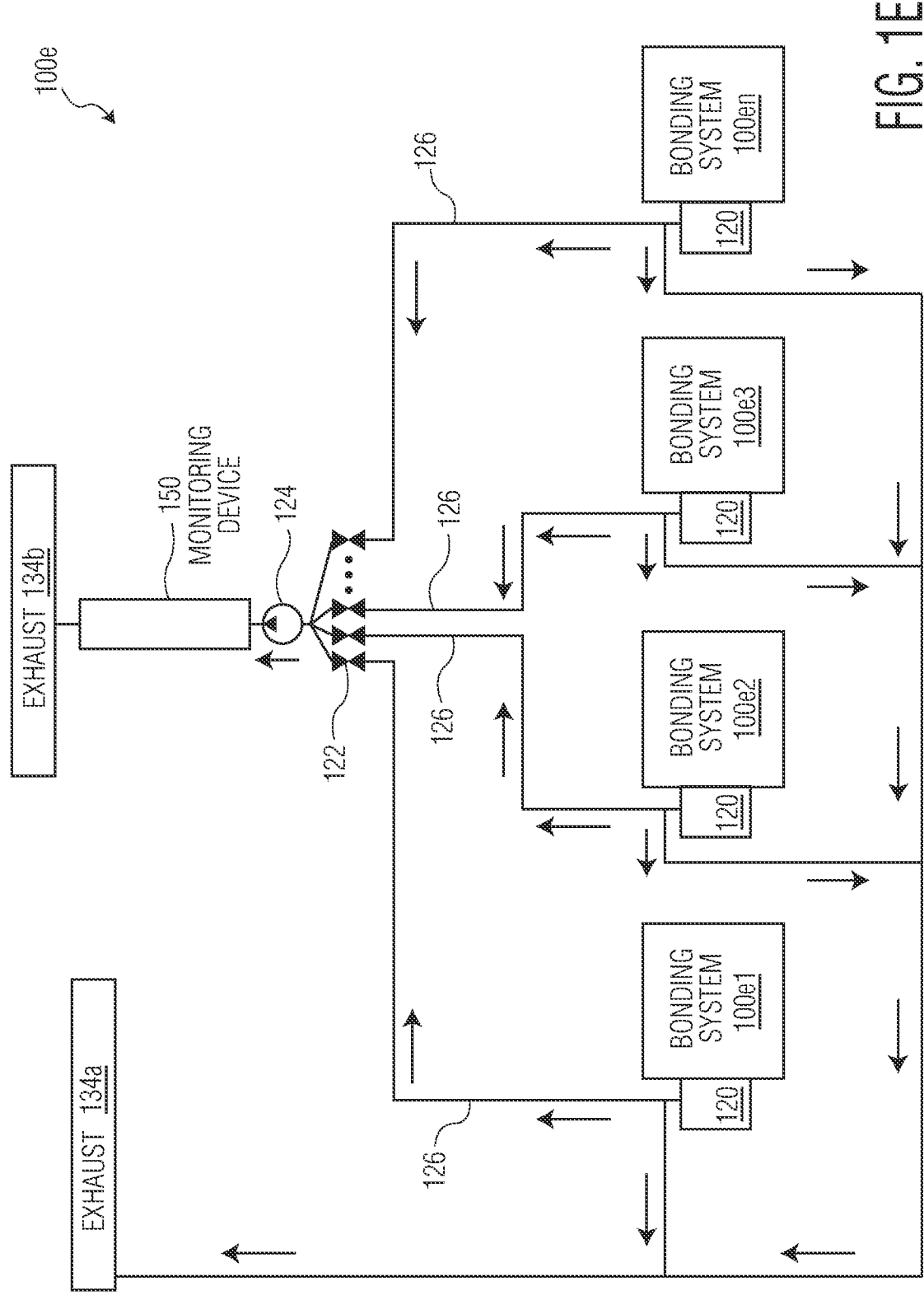

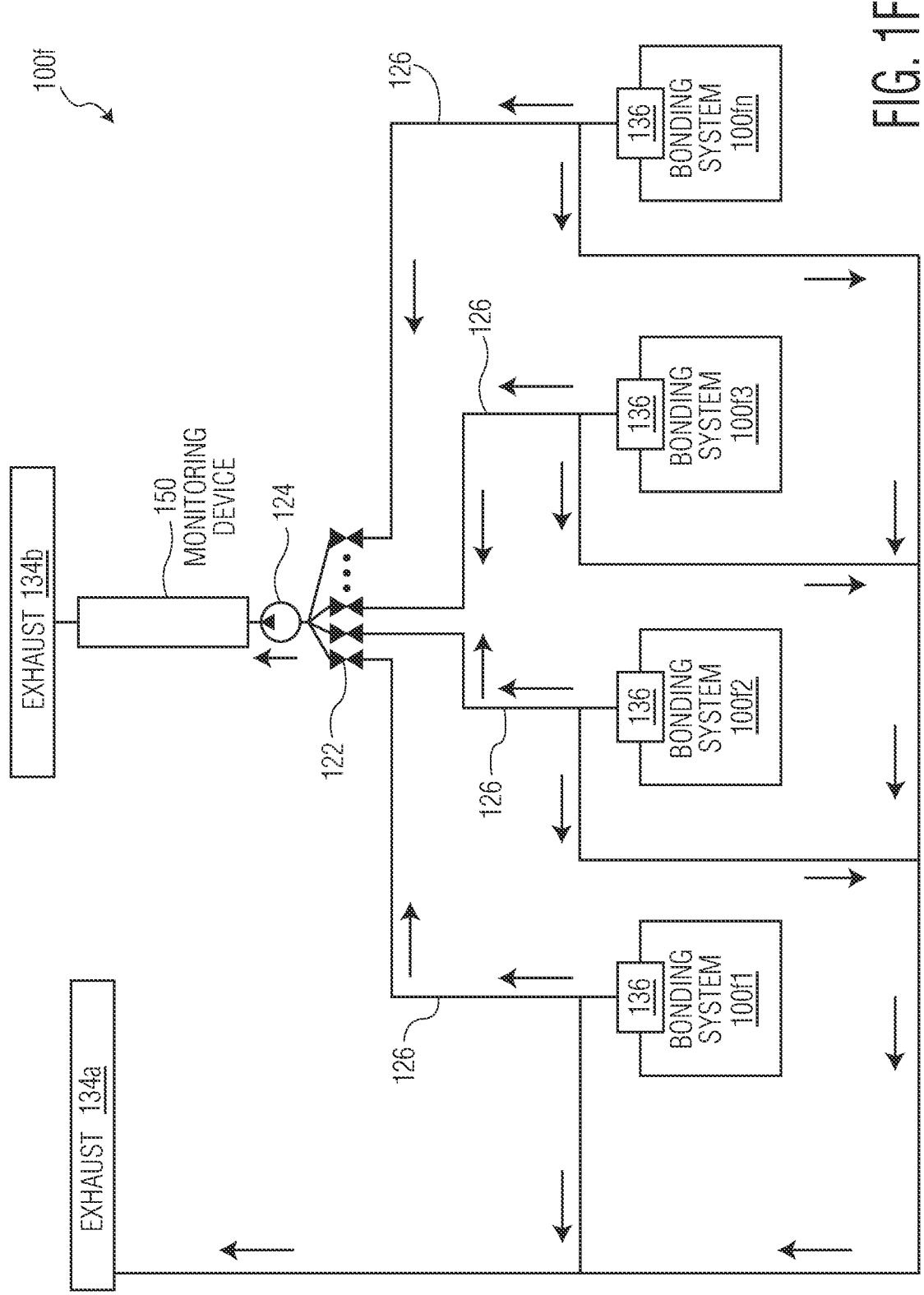

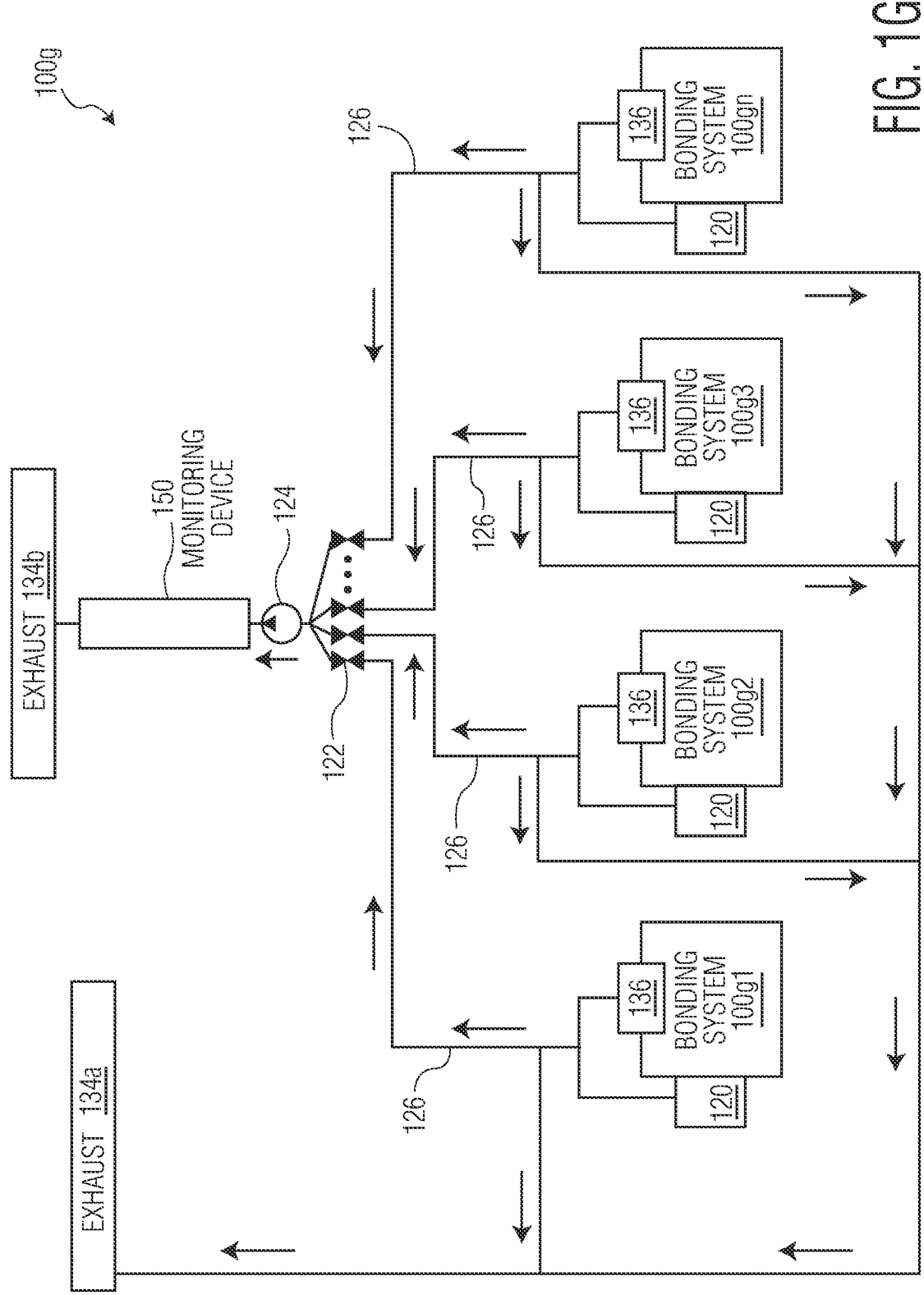

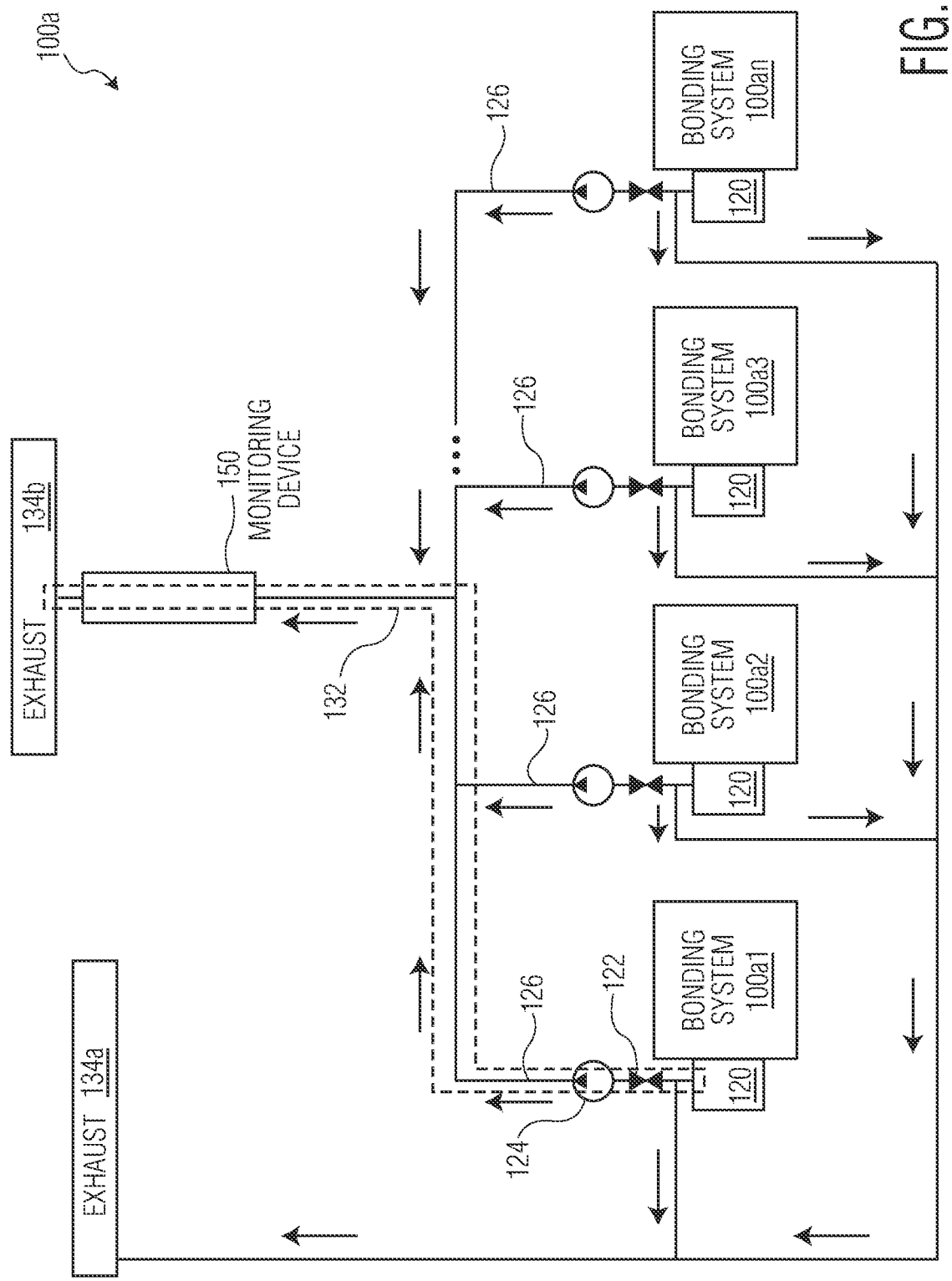

METHODS OF MONITORING GAS BYPRODUCTS OF A BONDING SYSTEM, AND RELATED MONITORING SYSTEMS AND BONDING SYSTEMS

CROSS-REFERENCE TO RELATED APPLICATION

This application claims the benefit of U.S. Provisional Application No. 63/311,018, filed on Feb. 16, 2022, the content of which is incorporated herein by reference.

FIELD

The invention relates to bonding processes and bonding systems, and more particularly, to improved methods of monitoring gas byproducts of such bonding systems.

BACKGROUND

Traditional semiconductor packaging typically involves die attach processes and wire bonding processes. Advanced semiconductor packaging technologies (e.g., flip chip bonding, thermocompression bonding, etc.) continue to gain traction in the industry. For example, in thermocompression bonding, heat and/or pressure (and sometimes ultrasonic energy) are used to form a plurality of interconnections between (i) electrically conductive structures on a semiconductor element and (ii) electrically conductive structures on a substrate.

In certain flip chip bonding or thermocompression bonding applications, the electrically conductive structures of the semiconductor element and/or the substrate may include conductive structures (e.g., copper pillars) that are subject to oxidation and/or other contamination. In such applications, it is desirable to provide an environment suitable for bonding. Conventionally, such an environment may be provided by using a reducing gas at a bonding area of the bonding system. The reducing gas reduces potential oxidation and/or contamination of the electrically conductive structures of the semiconductor element and/or the substrate.

In connection with such bonding systems, gas byproducts may be exhausted to the environment. It is desirable to monitor and/or control the amount of hazardous materials included in such gas byproducts.

Thus, it would be desirable to provide improved methods of monitoring gas byproducts of bonding systems, and related monitoring systems.

SUMMARY

According to an exemplary embodiment of the invention, a method of monitoring gas byproducts of a bonding system is provided. The method includes: (a) providing a plurality of bonding systems, each of the bonding systems including a reducing gas delivery system for use in connection with a bonding operation, each of the bonding systems being configured for exhausting gas byproducts; (b) connecting each of the bonding systems to a monitoring device using a respective gas delivery path; and (c) monitoring a composition of at least a portion of the gas byproducts with the monitoring device.

According to another exemplary embodiment of the invention, a monitoring system for monitoring gas byproducts of a plurality of bonding systems is provided. The monitoring system includes a plurality of bonding systems. Each of the bonding systems includes a reducing gas delivery system for use in connection with a bonding operation. Each of the bonding systems is configured for exhausting gas byproducts. The monitoring system also includes a monitoring device for monitoring a composition of at least a portion of the gas byproducts. The monitoring system also includes a plurality of connecting structures. Each of the connecting structures provides a gas delivery path between a respective one of the bonding systems and the monitoring device.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIGS. 1A-1I are block diagrams of various monitoring systems in accordance with multiple exemplary embodiments of the invention;

DETAILED DESCRIPTION

Figure 1A:
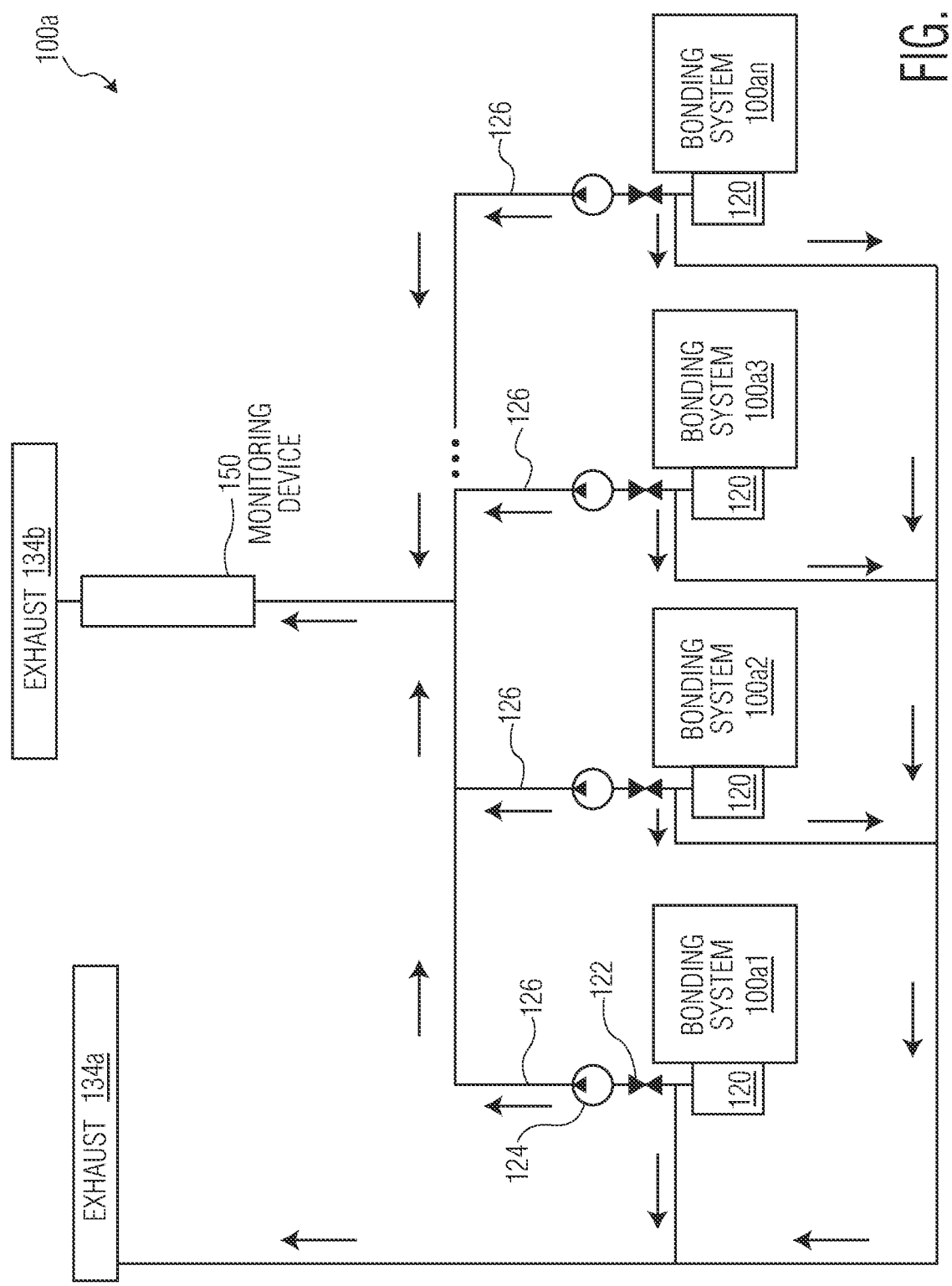

U.S. Pat. No. 10,861,820 (titled "METHODS OF BONDING SEMICONDUCTOR ELEMENTS TO A SUBSTRATE, INCLUDING USE OF A REDUCING GAS, AND RELATED BONDING MACHINES") and U.S. Pat. No. 11,205,633 (titled "METHODS OF BONDING OF SEMICONDUCTOR ELEMENTS TO SUBSTRATES, AND RELATED BONDING SYSTEMS") both relate to bonding systems utilizing reducing gas, and are incorporated by reference herein in their entirety.

As used herein, the term "semiconductor element" is intended to refer to any structure including (or configured to include at a later step) a semiconductor chip or die. Exemplary semiconductor elements include a bare semiconductor die, a semiconductor die on a substrate (e.g., a leadframe, a PCB, a carrier, a semiconductor chip, a semiconductor wafer, a BGA substrate, a semiconductor element, etc.), a packaged semiconductor device, a flip chip semiconductor device, a die embedded in a substrate, a stack of semiconductor die, amongst others. Further, the semiconductor element may include an element configured to be bonded or otherwise included in a semiconductor package (e.g., a spacer to be bonded in a stacked die configuration, a substrate, etc.).

As used herein, the term "substrate" is intended to refer to any structure to which a semiconductor element may be bonded. Exemplary substrates include, for example, a leadframe, a PCB, a carrier, a module, a semiconductor chip, a semiconductor wafer, a BGA substrate, another semiconductor element, etc.

As used herein, the term "bonding system" is intended to refer to any type of bonding machine (e.g., a thermocompression bonding machine, a flip chip bonding machine, a die attach system, etc.) that includes at least one bond head for bonding a semiconductor element to a substrate. It will be appreciated by those skilled in the art that certain bonding machines include a single bond head for bonding one semiconductor element at a time; however, other bonding machines may include a plurality of bond heads.

According to various exemplary embodiments of the invention, systems (and methods) are provided for sampling multiple bonding systems (e.g., reducing gas emission systems for multiple bonding systems) for determining a concentration of a certain compound (e.g., an acid compound, a hazardous acid compound, such as formic acid) using a single monitoring device. In a more specific example, an acidic compound is included in a reducing gas, and a single monitoring device may be used to measure the acid compound concentration (and/or other undesirable compound) emitted from an array of bonding systems (e.g., thermocompression bonders, flip chip bonders, etc.) in a gas byproduct.

In a specific exemplary embodiment, a formic acid concentration in an exhaust stream is measured using a Fourier-transform infrared spectroscope (FTIR) or other appropriate monitoring device. Such monitoring devices (e.g., measurement instruments) tend to be very expensive. According to the invention, a sampling interval rate for each bonding system can be configured to allowed multiple bonding systems to be monitored using a single monitoring device. This approach saves purchasing, operating, and maintenance costs (one monitoring device versus multiple monitoring devices). Further, using a single monitoring device removes certain issues related to unit to unit calibration uncertainty (of monitoring devices), and allows for a single instrument to provide data for multiple bonding systems.

According to certain exemplary embodiments of the invention, the monitoring device (e.g., an FTIR measurement instrument) can be used to identify unacceptable process conditions (e.g., an increased rate of formic acid emissions, or other relevant process emissions). In a specific example, acceptance criteria may be associated with each process condition monitored (e.g., an acid composition such as an acceptable part per million (PPM) level of an acid, such as formic acid, in an exhaust/emission). If the actual process condition monitored (e.g., acid composition in an exhaust) is above the acceptance criteria, then the monitoring system and/or the specific relevant bonding system may take an appropriate action. For example, the monitoring device may be in communication with each of the bonding systems. Thus, the monitoring device and/or the relevant bonding system (e.g., the bonding system with the unacceptable process condition, such as the acid PPM being too high in an exhaust) may produce an alarm, or adjust operation of a portion of the monitoring system (e.g., adjust the settings of the abatement system, adjust the settings of the reducing gas supply such as a fill level of the formic acid in a bubbler, etc.), or stop operation of the relevant bonding system.

Each of FIGS. 1A-1I illustrates a monitoring system (e.g., 100a, 100b, etc.) that includes a plurality of bonding systems (e.g., in FIG. 1A, bonding systems 100a1, 100a2, 100a3, . . . , 100an), a monitoring device 150, and a plurality of connecting structures 126. Each of the bonding systems includes a reducing gas delivery system (e.g., see the exemplary reducing gas delivery systems illustrated in FIG. 2 and FIG. 3) for use in connection with a bonding operation. Each of the bonding systems are configured for exhausting gas byproducts (e.g., see main exhaust 134a, and exhaust 134b, and associated connecting structures). Such gas byproducts may include unused and/or residual reducing gas, byproducts of oxide reduction using a reducing gas, etc.

Certain of the bonding systems (e.g., see FIGS. 1A, 1C, 1D, 1E, 1G, 1H and 1I) are illustrated being connected to an abatement system 120, through which gas byproducts are generated. Certain of the bonding systems (e.g., see FIGS. 1B, 1C, 1D, 1F, 1G, and 1H) utilize a machine exhaust system 136 to remove a reducing gas from an operational area of one of the bonding systems. Certain of the bonding systems (e.g., see FIGS. 1C, 1D, 1G, and 1H) include both the aforementioned abatement system 120 and the machine exhaust system 136.

After reducing gas (e.g., formic acid, acetic acid, etc.) is provided to a bonding area of bonding system (e.g., bonding system 100a1) (and perhaps used in connection with a bonding process), a gas byproduct is created. This gas byproduct may be produced by (i) abatement system 120 and/or (ii) machine exhaust system 136.

Abatement system 120 may abate a portion of a reducing gas (which may be considered toxic) by burning or otherwise changing the chemical structure. After processing by abatement system 120, a gas byproduct is the gaseous compound pulled from abatement system 120 towards main exhaust 134a and/or exhaust 134b. If such a gas byproduct from one of the bonding systems is to be sampled, the relevant valve 122 is opened, and the gas byproduct flows through the relevant connecting structure 126 (assisted by pump 124) toward exhaust 134b. This gas byproduct can then be sampled by monitoring device 150. The remaining gas byproduct is transported through piping or some other connecting structure to a main exhaust 134a.

Machine exhaust system 136 may continuously (or selectively) operate by pulling reducing gas away from an operational area of a bonding system. This operational area may be a much larger area than the bonding area of the bonding system. For example, the operational area may include a material handling area of the system, among other areas. By mixing this reducing gas with air (or some other gas) through the operation of machine exhaust system 136, another gas byproduct is created. If such a gas byproduct from a machine exhaust system 136 of one of the bonding systems is to be sampled, the relevant valve 122 is opened, and the gas byproduct flows through the relevant connecting structure 126 (assisted by pump 124) toward exhaust 134b. This gas byproduct can then be sampled by monitoring device 150. The remaining gas byproduct is transported through piping or some other connecting structure to a main exhaust 134a.

Through the various exemplary monitoring systems shown in FIGS. 1A-1I, a gas byproduct from an abatement system 120 and/or a machine exhaust system 136 may be sampled using monitoring device 150 (e.g., to monitor a composition of the gas byproduct, such as, to detect if an acceptable ppm level of an acid is present in the gas byproduct).

That is, each of the monitoring systems includes a monitoring device 150. Monitoring device 150 (e.g., a binary gas analyzer, a Fourier-transform infrared spectroscope (FTIR) gas analyzer, a mass spectrometer gas analyzer, a mass spectrometer in combination with a gas chromatograph, etc.) is configured to monitor a composition of a gas byproduct during operation of each of the bonding systems. Monitoring device 150 represents an analyzer including elements not shown, but required in certain applications, such as valves, pumps, flowmeters (e.g., mass flowmeters), etc.

Referring now to FIG. 1A, a monitoring system 100a is illustrated including bonding systems 100a1, 100a2, 100a3, . . . , 100an. Each of these bonding systems includes an abatement system 120, and relevant connecting structures 126 (e.g., piping, tubing, conduit, etc. providing a gas delivery path between each of the bonding systems and the monitoring device 150). Thus, in the embodiment shown in FIG. 1A, a gas byproduct from any of the abatement systems 120 may be sampled and monitored, using the illustrated valves 122, pumps 124, and connecting structures 126.

In a specific example, let us assume it is desired to sample and monitor a composition of a gas byproduct from abatement system 120 of bonding system 100*a*1. In such a case, valve 122 corresponding to bonding system 100*a*1 is open (while the other valves 122 corresponding to bonding systems 100*a*2, 100*a*3, . . . , 100*an* are closed). Thus, a single gas byproduct can be received and sampled by monitoring device 150. This gas byproduct follows a gas delivery path 132 as shown in FIG. 1I (where FIG. 1I illustrates monitoring system 100*a* from FIG. 1A, but highlighting a specific gas delivery path 132).

Figure 1B:
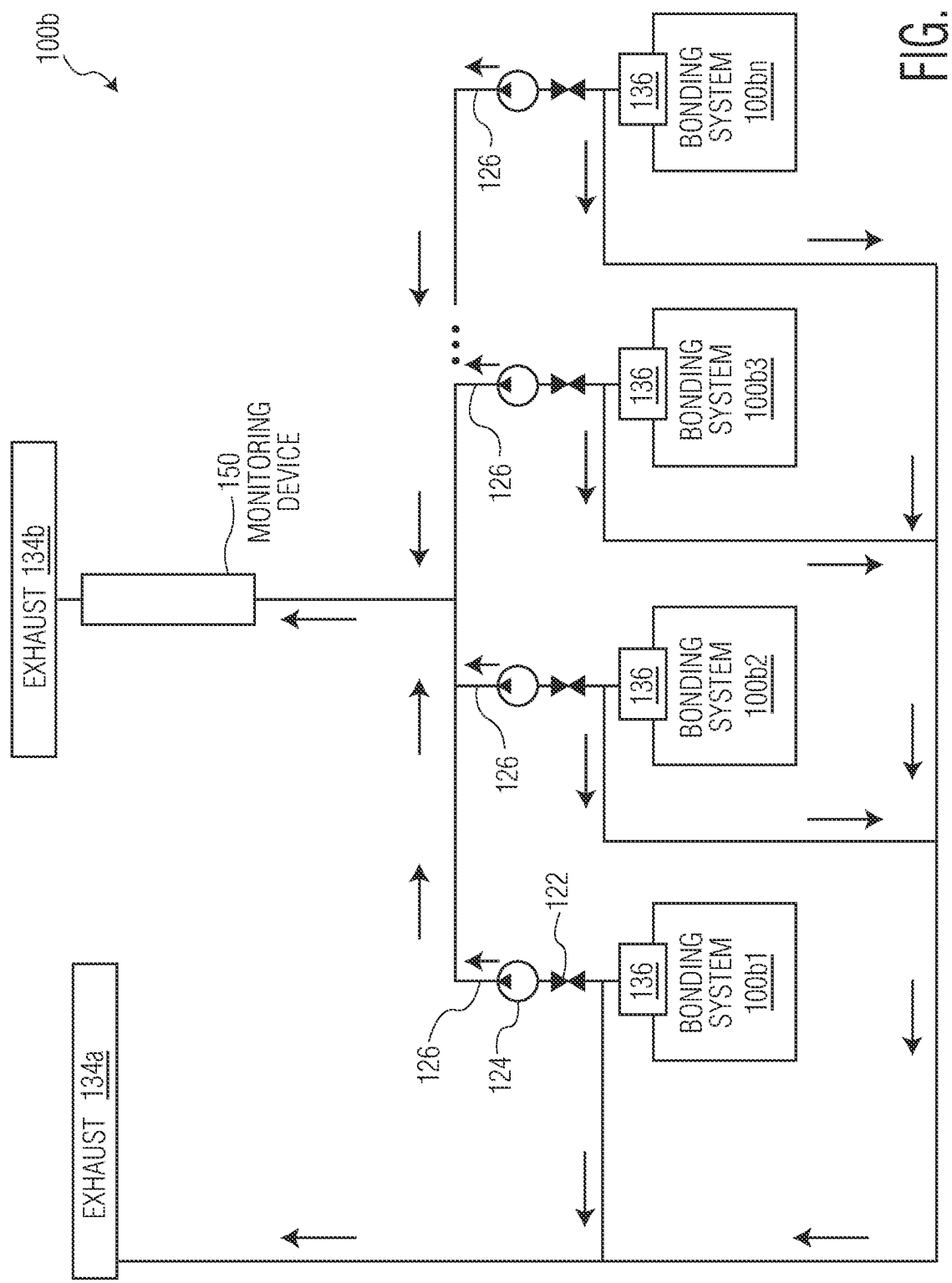

Referring now to FIG. 1B, a monitoring system 100*b* is illustrated including bonding systems 100*b*1, 100*b*2, 100*b*3, . . . , 100*bn*. Each of these bonding systems includes a machine exhaust system 136, and relevant connecting structures 126 (e.g., piping, tubing, conduit, etc. providing a gas delivery path between each of the bonding systems and the monitoring device 150). Thus, in the embodiment shown in FIG. 1B, a gas byproduct from any of the machine exhaust systems 136 may be sampled and monitored, using the illustrated valves 122, pumps 124, and connecting structures 126.

Figure 1C:
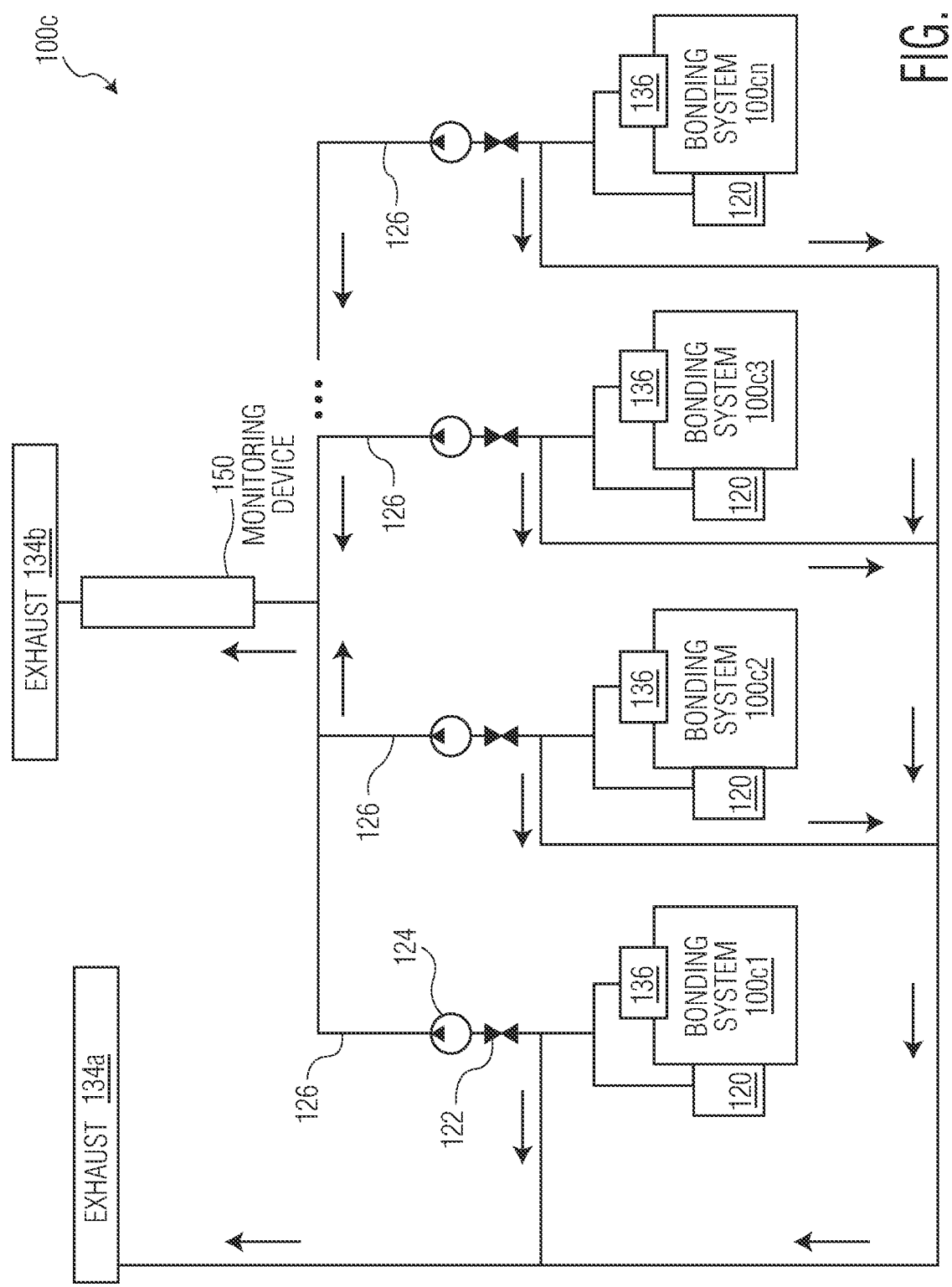

Referring now to FIG. 1C, a monitoring system 100*c* is illustrated including bonding systems 100*c*1, 100*c*2, 100*c*3, . . . , 100*cn*. Each of these bonding systems includes both an abatement system 120 and a machine exhaust system 136, and relevant connecting structures 126 (e.g., piping, tubing, conduit, etc. providing a gas delivery path between each of the bonding systems and the monitoring device 150). Thus, in the embodiment shown in FIG. 1C, a combined gas byproduct from respective pairs of abatement systems 120 and machine exhaust systems 136 may be sampled and monitored, using the illustrated valves 122, pumps 124, and connecting structures 126.

Figure 1D:
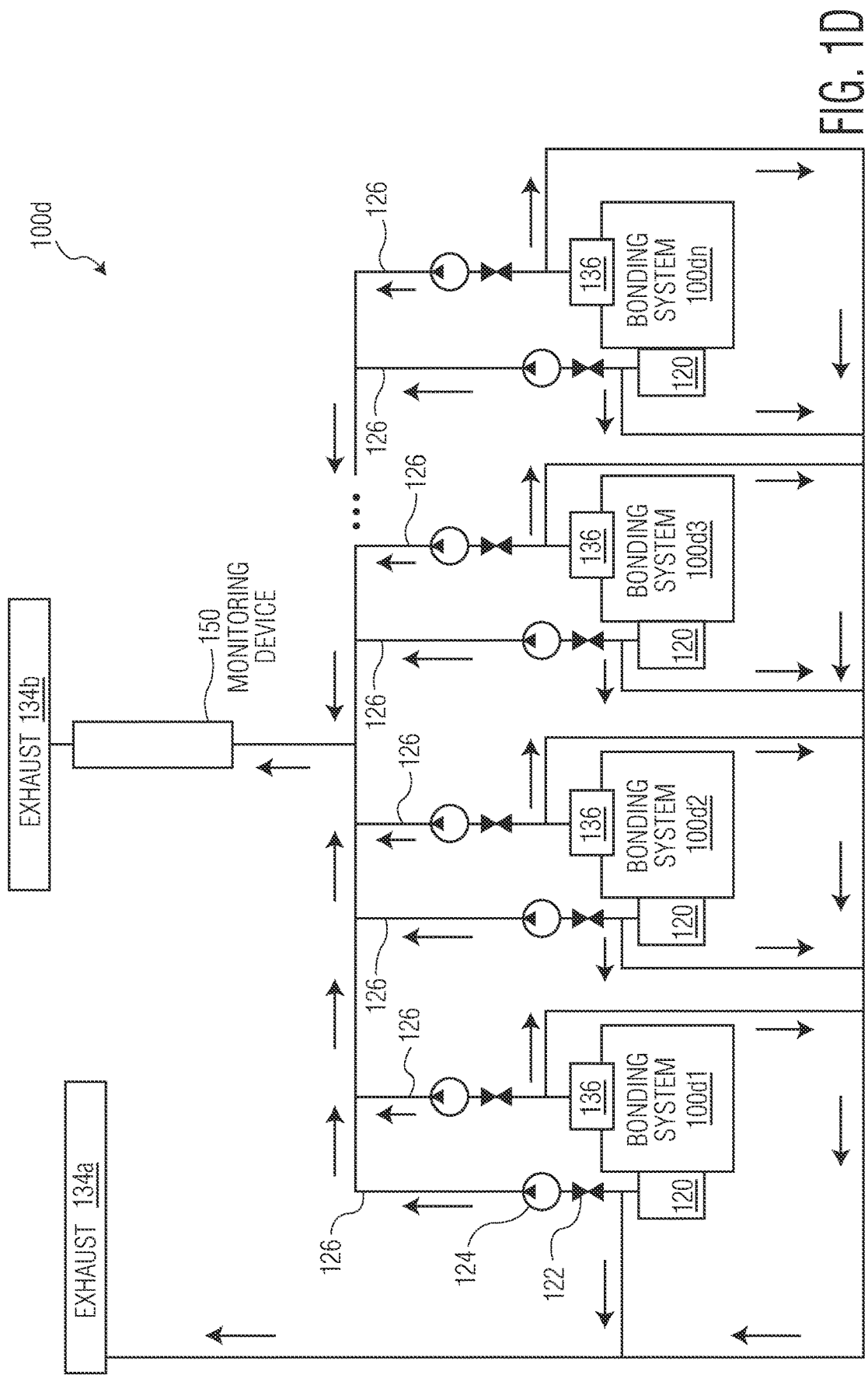
Figure 1H:
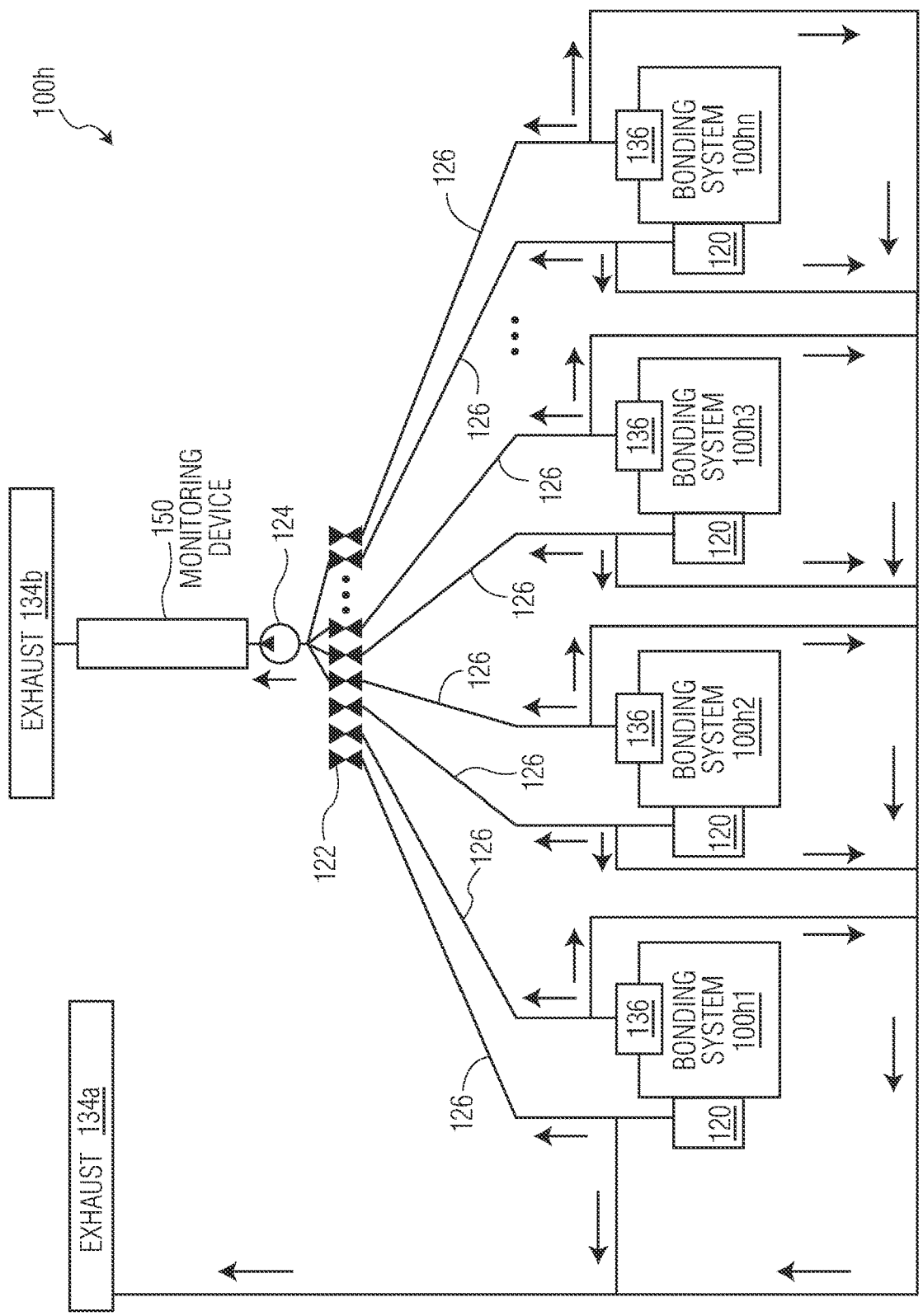

Referring now to FIG. 1D, a monitoring system 100*d* is illustrated including bonding systems 100*d*1, 100*d*2, 100*d*3, . . . , 100*dn*. Each of these bonding systems includes both an abatement system 120 and a machine exhaust system 136, and relevant connecting structures 126 (e.g., piping, tubing, conduit, etc. providing a gas delivery path between each of the bonding systems and the monitoring device 150). In contrast to FIG. 1C (where a combined gas byproduct from respective pairs of abatement systems 120 and machine exhaust systems 136 may be sampled and monitored), in the configuration of FIG. 1D, additional valves 122 and pumps 124 are provided such that a gas byproduct from any of the abatement systems 120 or machine exhaust systems 136 from any of the bonding systems may be sampled and monitored, using the illustrated valves 122, pumps 124, and connecting structures 126.

FIGS. 1E-1H illustrate monitoring systems 100*e*-100*h*. As opposed to the monitoring systems 100*a*-100*d* from FIGS. 1A-1D (where the valves 122 and pumps 124 are located at or adjacent the relevant bonding system), in monitoring systems 100*e*-100*h* the valves 122 (and a single pump 124) are located at, or adjacent, monitoring device 150. Thus, a single pump 124 may be utilized. Further, discrete/separate gas delivery paths are illustrated for each bonding system. Otherwise: monitoring system 100*e* (including bonding systems 100*e*1, 100*e*2, 100*e*3, . . . , 100*en*) is conceptually similar to monitoring system 100*a*; monitoring system 100*f* (including bonding systems 100*f*1, 100*f*2, 100*f*3, . . . , 100*fn*) is conceptually similar to monitoring system 100*b*; monitoring system 100*g* (including bonding systems 100*g*1, 100*g*2, 100*g*3, . . . , 100*gn*) is conceptually similar to monitoring system 100*c*; and monitoring system 100*h* (including bonding systems 100*h*1, 100*h*2, 100*h*3, . . . , 100*hn*) is conceptually similar to monitoring system 100*d*. Throughout this application, like reference numerals refer to like elements, unless indicated otherwise.

Figure 2:
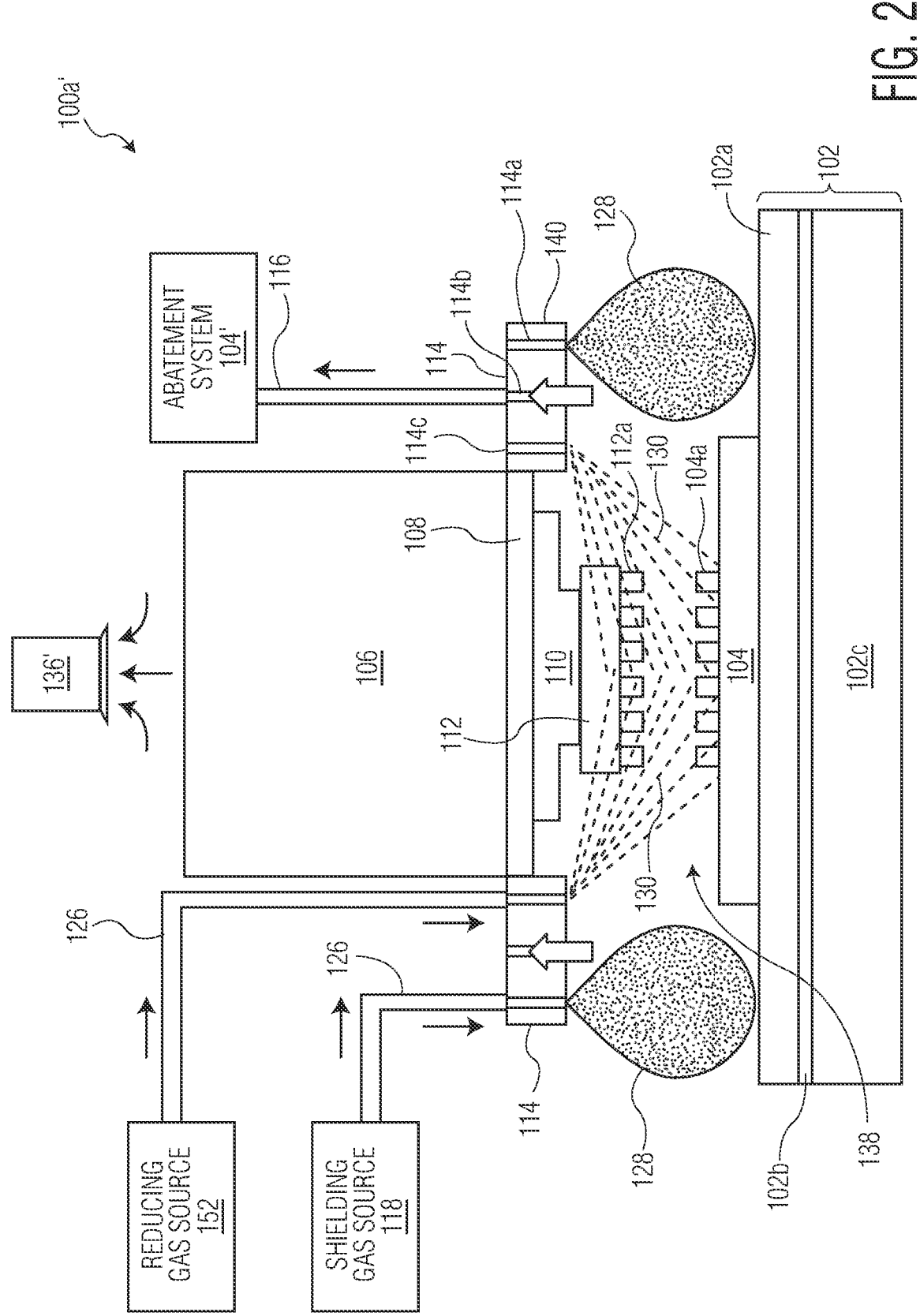
FIGS. 2 and 3 are block diagrams illustrating exemplary bonding systems which may be included in monitoring systems in accordance with multiple exemplary embodiments of the invention.

Referring now to FIG. 2, a bonding system 100*a*' is provided (e.g., a thermocompression bonding machine, a flip chip bonding machine, etc.) (where bonding system 100*a*' is an example that could be included as any bonding system in any of FIGS. 1A-1I). Bonding system 100*a*' includes a support structure 102 for supporting a substrate 104 during a bonding operation (where substrate 104 includes a plurality of electrically conductive structures 104*a*). Support structure 102 may include any appropriate structure for the specific application. In FIG. 2, support structure 102 includes top plate 102*a* (configured to directly support substrate 104), chuck 102*c*, and heater 102*b* disposed therebetween. In applications where heat for heating substrate 104 is desirable in connection with the bonding operation, a heater such as heater 102*b* may be utilized.

Bonding system 100*a*' also includes bond head assembly 106, which may be configured to move along (and about) a plurality of axes of bonding system 100 such as, for example, the x-axis, y-axis, z-axis, theta (rotative) axis, etc. Bond head assembly 106 includes a heater 108 and a bonding tool 110. That is, in certain bonding systems (e.g., thermocompression bonding machines) it may be desirable to heat the bonding tool. Thus, while FIG. 2 illustrates a separate heater 108 for heating bonding tool 110 (for heating semiconductor element 112 including a plurality of electrically conductive structures 112*a*), it will be appreciated that heater 108 and bonding tool 110 may be integrated into a single element (e.g., a heated bonding tool). FIG. 2 also illustrates an machine exhaust system 136' (which is an example of the machine exhaust systems 136 shown in FIGS. 1A-1I) for removing a reducing gas from an operational area of bonding system 100*a*'. From machine exhaust system 136', a gas byproduct may be sampled and monitored using a monitoring device 150 (e.g., see FIGS. 1A-1I).

In connection with a bonding operation, semiconductor element 112 is bonded to substrate 104 using bonding tool 110. During the bonding operation, corresponding ones of electrically conductive structures 112*a* are bonded (e.g., using heat, force, ultrasonic energy, etc.) to respective ones of electrically conductive structures 104*a*.

In certain bonding applications (e.g., flip chip and/or thermocompression bonding), it is desirable to provide an environment suitable for bonding. Conventionally, such an environment may be provided by using a reducing gas at the bonding area to reduce potential contamination of the electrically conductive structures of the semiconductor element or the substrate to which it will be bonded.

Bonding system 100*a*' also includes a reducing gas delivery system 140 for providing a reducing gas 130 to a bonding area 138 during bonding of semiconductor element 112 to substrate 104. Reducing gas delivery system 140 is illustrated as being integrated with bond head assembly 106. Reducing gas delivery system 140 includes a bond head manifold 114 (carried by bond head assembly 106) for receiving and distributing fluids (e.g., gases, vapors, etc.) as desired in the given application. A reducing gas source 152 (e.g., piping from a source, a bubbler type system, etc.) provides a reducing gas to bond head manifold 114 of reducing gas delivery system 140. The reducing gas typically includes a carrier gas and an acid (e.g., formic acid, acetic acid, etc.). For example, the reducing gas may be a saturated vapor gas.

In FIG. 2, while bond head manifold 114 is illustrated in a cross-sectional view, the actual bond head manifold 114 surrounds bonding tool 110 (e.g., bond head manifold 114 surrounds bonding tool 110 in a coaxial configuration). Of course, bond head manifold 114 may have different configurations from that shown in FIG. 2. Further, it is understood that certain details of bond head manifold 114 (e.g., structural details for distributing a reducing gas within bond head manifold 114, structural details for distributing a shielding gas within bond head manifold 114, structural details for drawing a vacuum through a center channel of bond head manifold 114 with a vacuum system, etc.) are omitted for simplicity.

Bond head manifold 114 includes three channels 114a, 114b, 114c having different functions. Outer channel 114a receives a shielding gas 128 (e.g., nitrogen gas) from shielding gas source 118. That is, a shielding gas 128 is provided from shielding gas source 118 (e.g., a nitrogen gas supply), through connecting structure 126 (where connecting structure 126 may include hard piping, flexible tubing, a combination of both, or any other structure adapted to carry the fluids described herein), to outer channel 114a of bond head manifold 114. From outer channel 114a of bond head manifold 114, the shielding gas 128 is provided as a shield from the outside environment. Inner channel 114c receives a reducing gas 130 (e.g., where the reducing gas is a saturated vapor gas) from reducing gas source 152, and provides reducing gas 130 in the area of semiconductor element 112 and substrate 104 in connection with a bonding operation.

After reducing gas 130 is distributed in the area of semiconductor element 112 and substrate 104, reducing gas 130 contacts surfaces of each of electrically conductive structures 104a and electrically conductive structures 112a. The surfaces of electrically conductive structures 104a/112a may then include a reaction product (e.g., where the reaction product is provided as a result of (i) a surface oxide on electrically conductive structures 104a/112a, and (ii) reducing gas 130 (and possibly heat provided by heater 108 and transferred to electrically conductive structures 104a via contact with electrically conductive structures 112a, if desired)). This reaction product is desirably removed from the bonding area 138 (i.e., the area where electrically conductive structures 112a of semiconductor element 112 are bonded to corresponding electrically conductive structures 104a of substrate 104) using vacuum provided through center channel 114b of bond head manifold 114 via exit piping 116.

Semiconductor element 112 (carried by bond head assembly 106) is illustrated positioned above substrate 104. More specifically, FIG. 2 illustrates reducing gas 130 being provided at the bonding area 138, as well as shielding gas 128 being provided, and vacuum being drawn through center channel 114b of bond head manifold 114 by a vacuum system via exit piping 116. Thus, the flow of reducing gas 130 reaches desired portions of semiconductor element 112 and substrate 104 (e.g., electrically conductive structures 104a and electrically conductive structures 112a) for: removing contaminants from the electrically conductive structures 104a and electrically conductive structures 112a; and/or shielding electrically conductive structures 104a and electrically conductive structures 112a from further potential contamination.

Also illustrated in FIG. 2, respective ones of electrically conductive structures 112a (of semiconductor element 112) are aligned with ones of electrically conductive structures 104a (of substrate 104). In subsequent steps (not illustrated), the process proceeds to a bonding step (e.g., a thermocompression bonding step), for example, through the lowering of bond head assembly 106. That is, electrically conductive structures 112a are bonded to corresponding electrically conductive structures 104a. This bonding process may be a thermocompression bonding process (e.g., including heat and/or bond force, where the bond force may be a higher bond force such as 50-300 N), and may also include ultrasonic energy transfer (e.g., from an ultrasonic transducer included in bond head assembly 106).

FIG. 2 also illustrates an abatement system 104' (which is an example of the abatement systems 120 shown in FIGS. 1A-1I) for receiving a reducing gas from the vacuum channel of reducing gas delivery system 140. From abatement system 104', a gas byproduct is created which may be sampled and monitored using a monitoring device 150 (e.g., see FIGS. 1A-1I).

Although FIG. 2 illustrates bond head manifold 114, integrated with the bond head assembly 106, for: delivering the reducing gas; delivering the shielding gas; and providing vaccum—the invention is not limited thereto. For example, instead of such functions being provided through integration of a manifold with the bond head assembly, such functions may be provided through integration with a support structure for supporting the substrate (e.g., see FIG. 3). Further, such functions may be split between the bond head assembly and the support structure (andaF possibly other structures of the bonding system).

Figure 3:
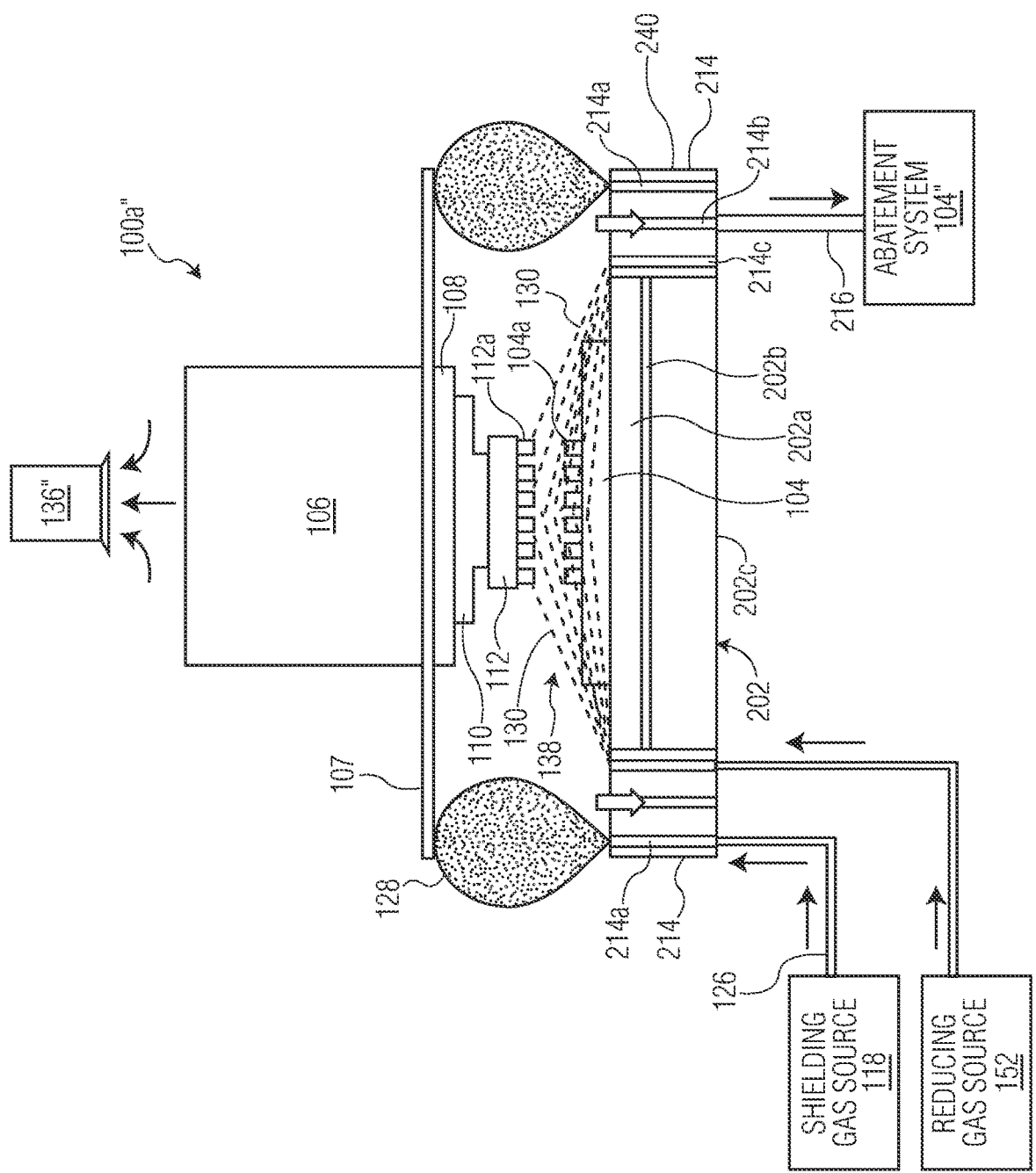

FIG. 3 is a block diagram of a bonding system 100a''', with certain similar elements and functions to that illustrated and described with respect to FIG. 2, except that the manifold functions (delivering the reducing gas; delivering the shielding gas; and providing vacuum) are integrated into a support structure 202.

FIG. 3 illustrates bonding system 100a'' (where bonding system 100a'' is an example that could be included as any bonding system in any of FIGS. 1A-1I) (e.g., a thermocompression bonding machine, a flip chip bonding machine, etc.). Bonding machine 100a'' includes a support structure 202 for supporting a substrate 104 during a bonding operation (where substrate 104 includes a plurality of electrically conductive structures 104a). Support structure 202 may include any appropriate structure for the specific application. In FIG. 3, support structure 202 includes top plate 202a (configured to directly support substrate 104), chuck 202c, and heater 202b disposed therebetween. In applications where heat for heating substrate 104 is desirable in connection with the bonding operation, a heater such as heater 202b may be utilized.

FIG. 3 also illustrates bond head assembly 106 (including heater 108 and bonding tool 110), which may be configured to move along (and about) a plurality of axes of bonding system 100a'' such as, for example, the x-axis, y-axis, z-axis, theta (rotative) axis, etc. In FIG. 3, bond head assembly 106 carries a plate 107 for partially containing at least one of shielding gas 128 and reducing gas 130 (see description below). FIG. 3 also illustrates a machine exhaust system 136'' (which is an example of the machine exhaust system 136 shown in FIGS. 1A-1I) for removing a reducing gas from an operational area (including bonding area 138) of bonding system 100a''. From machine exhaust system 136'', a gas byproduct may be sampled and monitored using a monitoring device 150 (e.g., see FIGS. 1A-1I).

Bonding system 100a" includes a reducing gas delivery system 240 for providing a reducing gas 130 to a bonding area 138 during bonding of semiconductor element 112 to substrate 104. Reducing gas delivery system 240 is illustrated as being integrated with support structure 202. As opposed to a bond head manifold 114 carried by bond head assembly 106 (as in FIG. 2), FIG. 3 illustrates a manifold 214 carried by, and/or integrated with, support structure 202. Manifold 214 is configured for receiving and distributing fluids (e.g., gases, vapors, etc.) as desired in the given application. In FIG. 3, while manifold 214 is illustrated in a cross-sectional view, the actual manifold 214 at least partially surrounds substrate 104. Of course, manifold 214 may have different configurations from that shown in FIG. 3. Further, it is understood that certain details of manifold 214 (e.g., structural details for distributing reducing gas 130 within manifold 214, structural details for distributing shielding gas 128 within manifold 214, structural details for drawing a vacuum through a center channel of manifold 214 by a vacuum system, etc.) are omitted for simplicity.

Manifold 214 includes three channels 214a, 214b, 214c having different functions. Outer channel 214a receives shielding gas 128 (e.g., nitrogen gas) from a shielding gas source 118. From outer channel 214a of manifold 214, shielding gas 128 is provided as a shield from the outside environment. Inner channel 214c receives a reducing gas 130 (e.g., where the reducing gas is a saturated vapor gas) from a reducing gas source 152 and provides reducing gas 130 in the area of semiconductor element 112 and substrate 104 in connection with a bonding operation.

After reducing gas 130 is distributed in the area of semiconductor element 112 and substrate 104, reducing gas 130 contacts surfaces of each of electrically conductive structures 104a and electrically conductive structures 112a. The surfaces of electrically conductive structures 104a/112a may then include a reaction product (e.g., where the reaction product is provided as a result of: (i) a surface oxide on electrically conductive structures 104a/112a, and (ii) reducing gas 130 (and possibly heat provided by heater 108, if desired)). This reaction product is desirably removed from the bonding area 138 (i.e., the area where electrically conductive structures 112a of semiconductor element 112 are bonded to corresponding electrically conductive structures 104a of substrate 104) using vacuum provided through center channel 214b of manifold 214 via exit piping 216.

Referring to FIG. 3, semiconductor element 112 (carried by bond head assembly 106) is positioned above substrate 104. FIG. 3 illustrates reducing gas 130 being provided at the bonding area 138, as well as shielding gas 128 being provided, and vacuum being drawn through center channel 214b of bond head manifold 214 by a vacuum system via exit piping 216 into abatement system 104". Thus, the flow of reducing gas 130 reaches desired portions of semiconductor element 112 and substrate 104 (e.g., electrically conductive structures 104a and electrically conductive structures 112a) for: removing contaminants from the electrically conductive structures 104a and electrically conductive structures 112a; and/or shielding electrically conductive structures 104a and electrically conductive structures 112a from further potential contamination.

Also illustrated in FIG. 3, respective ones of electrically conductive structures 112a (of semiconductor element 112) are aligned with ones of electrically conductive structures 104a (of substrate 104). In subsequent steps, the process proceeds to a bonding step (e.g., a thermocompression bonding step), for example, through the lowering of bond head assembly 106. That is, electrically conductive structures 112a are bonded to corresponding electrically conductive structures 104a. This may be through a thermocompression bonding process (e.g., including heat and/or bond force, where the bond force may be a higher bond force such as 50-300 N), and may also include ultrasonic energy transfer (e.g., from an ultrasonic transducer included in bond head assembly 106).

FIG. 3 also illustrates an abatement system 104" (which is an example of the abatament systems 104 shown in FIGS. 1A-1I) for receiving a reducing gas from the vacuum channel of reducing gas delivery system 240. From abatement system 104", a gas byproduct is created which may be sampled and monitored using a monitoring device 150 (e.g., see FIGS. 1A-1I).

Figure 4:
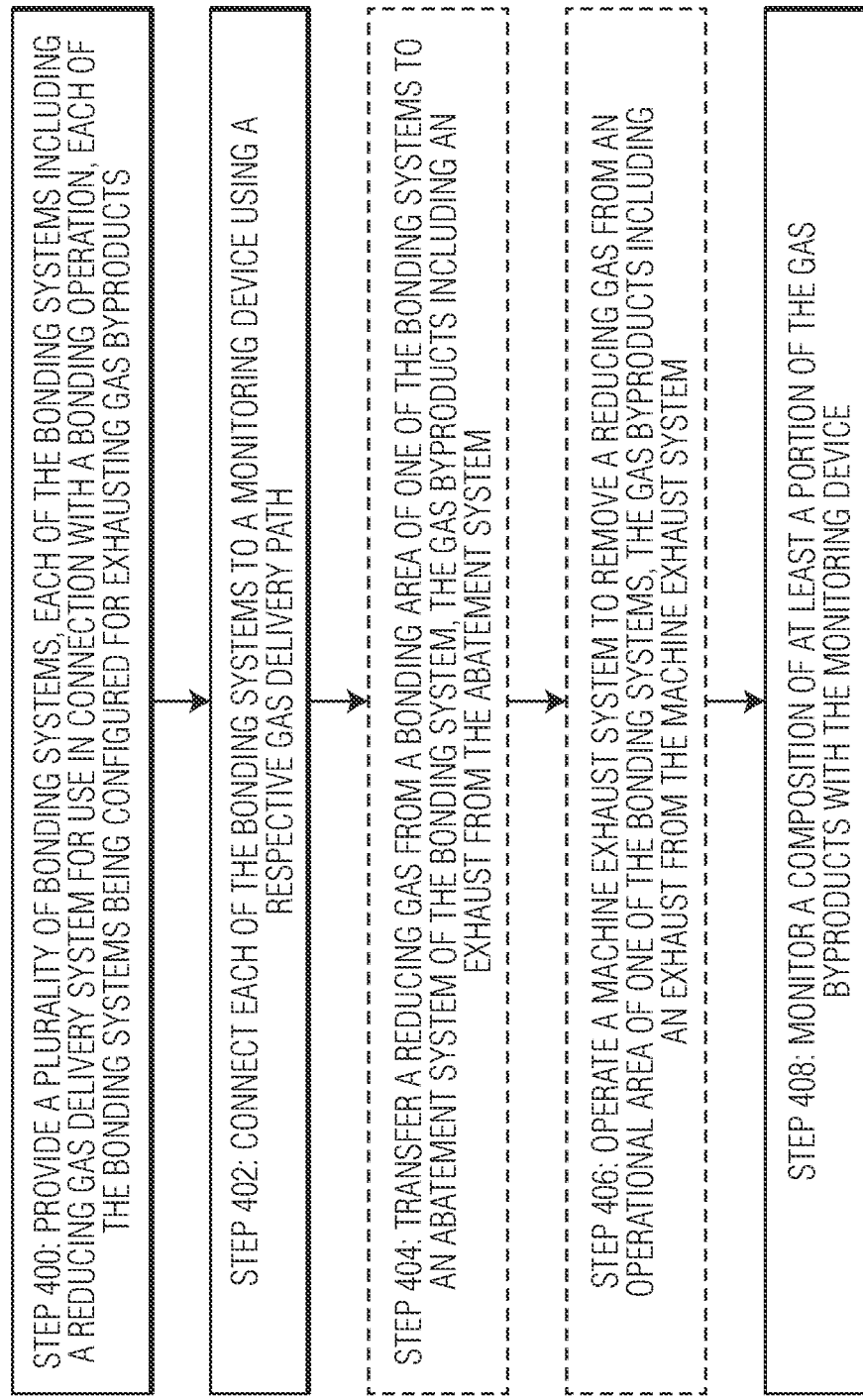
FIG. 4 is a flow diagram illustrating a method of monitoring gas byproducts of a bonding system in accordance with an exemplary embodiment of the invention.

FIG. 4 is a flow diagram illustrating a method of monitoring gas byproducts of a bonding system. As is understood by those skilled in the art, certain steps included in the flow diagrams may be omitted; certain additional steps may be added; and the order of the steps may be altered from the order illustrated—all within the scope of the invention.

Referring specifically to FIG. 4, at Step 400, a plurality of bonding systems are provided (e.g., see the plurality of bonding systems in any of FIGS. 1A-1I). Each of the bonding systems include a reducing gas delivery system for use in connection with a bonding operation. Further, each of the bonding systems are configured for exhausting gas byproducts. At Step 402, each of the bonding systems are connected to a monitoring device (e.g., see monitoring device 150 in each of FIGS. 1A-1I) using a respective gas delivery path. At optional Step 404, a reducing gas is transferred from a bonding area of one of the bonding systems to an abatement system of the bonding system. The gas byproducts in optional Step 404 include an exhaust from the abatement system. At optional Step 406, a machine exhaust system is operated to remove a reducing gas from an operational area of one of the bonding systems. The gas byproducts in optional Step 406 include an exhaust from the machine exhaust system. At Step 408, a composition of at least a portion of the gas byproducts are monitored with the monitoring device.

Although the present application is described primarily with respect sampling gas byproducts provided using an abatement system and/or a machine exhaust system, it is not limited thereto. Other gas byproducts may be produced on bonding systems which may be monitored within the scope and spirit of the invention.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method of monitoring gas byproducts of a bonding system, the method comprising the steps of:
   (a) providing a plurality of bonding systems, each of the bonding systems including a reducing gas delivery system for use in connection with a bonding operation, each of the bonding systems being configured for exhausting gas byproducts;
   (b) connecting each of the bonding systems to a monitoring device using a respective gas delivery path, the gas delivery path between each of the plurality of bonding systems and the monitoring device including a valve such that the monitoring device is configured to selectively monitor a composition of at least a portion of the gas byproducts with the monitoring device with respect to any one of the bonding systems; and (c) monitoring the composition of at least a portion of the gas byproducts with the monitoring device.

2. The method of claim 1 wherein the reducing gas delivery system provides a reducing gas including a carrier gas and an acid.

3. The method of claim 2 wherein the acid includes at least one of formic acid and acetic acid.

4. The method of claim 2 wherein the reducing gas is a saturated vapor gas.

5. The method of claim 2 wherein the reducing gas includes an acid compound, and wherein step (c) includes monitoring the composition of at least the portion of the gas byproducts to determine a concentration of the acid compound.

6. The method of claim 1 wherein each of the bonding systems includes a bond head assembly configured for use with a bonding tool, the bonding tool being configured to carry a semiconductor element including a plurality of first electrically conductive structures, the bonding tool being configured to bond the semiconductor element to a substrate in connection with the bonding operation, the substrate including a plurality of second electrically conductive structures, wherein the reducing gas delivery system provides a reducing gas to contact each of the plurality of first electrically conductive structures and the plurality of second electrically conductive structures via a manifold integrated with the bond head assembly.

7. The method of claim 1 wherein each of the bonding systems includes a bond head assembly configured for use with a bonding tool, the bonding tool being configured to carry a semiconductor element including a plurality of first electrically conductive structures, the bonding tool being configured to bond the semiconductor element to a substrate in connection with the bonding operation, the substrate including a plurality of second electrically conductive structures, the substrate being supported by a support structure during the bonding operation, wherein the reducing gas delivery system provides a reducing gas to contact each of the plurality of first electrically conductive structures and the plurality of second electrically conductive structures via a manifold integrated with the support structure.

8. The method of claim 1 wherein the monitoring device includes at least one of (i) a binary gas analyzer, (ii) a Fourier-transform infrared spectroscope (FTIR) gas analyzer, (iii) a mass spectrometer gas analyzer, and (iv) a mass spectrometer in combination with a gas chromatograph.

9. The method of claim 1 further comprising the step of transferring a reducing gas from a bonding area of one of the bonding systems to an abatement system of the bonding system, the gas byproducts including an exhaust from the abatement system.

10. The method of claim 9 wherein the step of transferring includes transferring the reducing gas from the bonding area to the abatement system using a vacuum system integrated with a bond head assembly of the bonding system.

11. The method of claim 9 wherein the step of transferring includes transferring the reducing gas from the bonding area to the abatement system using a vacuum system integrated with a support structure of the bonding system.

12. The method of claim 1 further comprising the step of operating a machine exhaust system to remove a reducing gas from an operational area of one of the bonding systems, the gas byproducts including an exhaust from the machine exhaust system.

13. A monitoring system for monitoring gas byproducts of a plurality of bonding systems, the monitoring system comprising:
a plurality of bonding systems, each of the bonding systems including a reducing gas delivery system for use in connection with a bonding operation, each of the bonding systems being configured for exhausting gas byproducts;
a monitoring device for monitoring a composition of at least a portion of the gas byproducts; and
a plurality of connecting structures, each of the connecting structures providing a gas delivery path between a respective one of the plurality of bonding systems and the monitoring device, the respective gas delivery path between each of the plurality of bonding systems and the monitoring device including a valve such that the monitoring device is configured to selectively monitor the composition with respect to any one of the bonding systems.

14. The monitoring system of claim 13 wherein the reducing gas delivery system is configured to provide a reducing gas including a carrier gas and an acid.

15. The monitoring system of claim 14 wherein the acid includes at least one of formic acid and acetic acid.

16. The monitoring system of claim 14 wherein the reducing gas is a saturated vapor gas.

17. The monitoring system of claim 14 wherein the reducing gas includes an acid compound, and wherein the monitoring device is configured to monitor the composition of at least a portion of the gas byproducts to determine a concentration of the acid compound.

18. The monitoring system of claim 13 wherein each of the bonding systems includes a bond head assembly configured for use with a bonding tool, the bonding tool being configured to carry a semiconductor element including a plurality of first electrically conductive structures, the bonding tool being configured to bond the semiconductor element to a substrate in connection with the bonding operation, the substrate including a plurality of second electrically conductive structures, wherein the reducing gas delivery system provides a reducing gas to contact each of the plurality of first electrically conductive structures and the plurality of second electrically conductive structures via a manifold integrated with the bond head assembly.

19. The monitoring system of claim 13 wherein each of the bonding systems includes a bond head configured for use with a bonding tool, the bonding tool being configured to carry a semiconductor element including a plurality of first electrically conductive structures, the bonding tool being configured to bond the semiconductor element to a substrate in connection with the bonding operation, the substrate including a plurality of second electrically conductive structures, the substrate being supported by a support structure during the bonding operation, wherein the reducing gas delivery system provides a reducing gas to contact each of the plurality of first electrically conductive structures and the plurality of second electrically conductive structures via a manifold integrated with the support structure.

20. The monitoring system of claim 13 wherein the monitoring device includes at least one of (i) a binary gas analyzer, (ii) a Fourier-transform infrared spectroscope (FTIR) gas analyzer, (iii) a mass spectrometer gas analyzer, and (iv) a mass spectrometer in combination with a gas chromatograph.

21. The monitoring system of claim 13 wherein each of the bonding systems is configured to transfer a reducing gas from a bonding area of the bonding system to an abatement system of the bonding system, the gas byproducts including an exhaust from the abatement system.

22. The monitoring system of claim 21 wherein the bonding system is configured to transfer the reducing gas from the bonding area to the abatement system using a vacuum system integrated with a bond head assembly of the bonding system.

23. The monitoring system of claim 21 wherein the bonding system is configured to transfer the reducing gas from the bonding area to the abatement system using a vacuum system integrated with a support structure of the bonding system.

24. The monitoring system of claim 13 wherein each of the plurality of bonding systems includes a machine exhaust system to remove a reducing gas from an operational area of the bonding system, the gas byproducts including an exhaust from the machine exhaust system.

25. A method of monitoring gas byproducts of a bonding system, the method comprising the steps of:
 (a) providing a plurality of bonding systems, each of the bonding systems including a reducing gas delivery system for use in connection with a bonding operation, each of the bonding systems being configured for exhausting gas byproducts, each of the bonding systems including an abatement system, the gas byproducts including an exhaust from the abatement system;
 (b) connecting each of the bonding systems to a monitoring device using a respective gas delivery path;
 (c) monitoring a composition of at least a portion of the gas byproducts with the monitoring device; and
 (d) transferring a reducing gas from a bonding area of one of the bonding systems to the abatement system of the one of the bonding systems using a vacuum system of the one of the bonding systems, the vacuum system being integrated with a bond head assembly or a support structure of the one of the bonding systems.

26. A monitoring system for monitoring gas byproducts of a plurality of bonding systems, the monitoring system comprising:
 a plurality of bonding systems, each of the bonding systems including a reducing gas delivery system for use in connection with a bonding operation, each of the bonding systems being configured for exhausting gas byproducts, each of the bonding systems being configured to transfer a reducing gas from a bonding area of the bonding system to an abatement system of the bonding system using a vacuum system of the bonding system, the vacuum system being integrated with a bond head assembly or a support structure of the bonding system, the gas byproducts including an exhaust from the abatement system;
 a monitoring device for monitoring a composition of at least a portion of the gas byproducts; and
 a plurality of connecting structures, each of the connecting structures providing a gas delivery path between a respective one of the plurality of bonding systems and the monitoring device.

\* \* \* \* \*